(12) United States Patent
Okazoe et al.

(10) Patent No.: US 7,053,237 B2
(45) Date of Patent: May 30, 2006

(54) PROCESS FOR PRODUCING A FLUORINATED ESTER, A FLUORINATED ACYL FLUORIDE AND A FLUORINATED VINYL ETHER

(75) Inventors: Takashi Okazoe, Yokohama (JP); Kunio Watanabe, Yokohama (JP); Shin Tatematsu, Yokohama (JP); Hidenobu Murofushi, Yokohama (JP); Masakuni Sato, Yokohama (JP); Masahiro Ito, Yokohama (JP); Koichi Yanase, Ichihara (JP); Yasuhiro Suzuki, Ichihara (JP)

(73) Assignee: Asahi Glass Company, Limited, Tokyo (JP)

( * ) Notice: Subject to any disclaimer, the term of this patent is extended or adjusted under 35 U.S.C. 154(b) by 52 days.

(21) Appl. No.: 10/619,784

(22) Filed: Jul. 16, 2003

(65) Prior Publication Data
US 2005/0261516 A1 Nov. 24, 2005

Related U.S. Application Data

(63) Continuation of application No. PCT/JP02/00236, filed on Jan. 16, 2002.

(30) Foreign Application Priority Data
Jan. 16, 2001 (JP) ............................. 2001-008252

(51) Int. Cl.
C07C 69/63 (2006.01)
C07C 41/00 (2006.01)
(52) U.S. Cl. ....................................... 560/227; 568/685
(58) Field of Classification Search ................ 560/227
See application file for complete search history.

(56) References Cited

U.S. PATENT DOCUMENTS

| | | |
|---|---|---|
| 3,114,778 A | 12/1963 | Fritz et al. |
| 3,900,372 A | 8/1975 | Childs et al. |
| 4,524,032 A | 6/1985 | Misaki et al. |
| 4,526,948 A | 7/1985 | Resnick |
| 4,868,318 A | 9/1989 | Scherer, Jr. et al. |
| 4,996,369 A | 2/1991 | Kalota et al. |
| 5,093,432 A | 3/1992 | Bierschenk et al. |
| 5,322,903 A | 6/1994 | Bierschenk et al. |
| 5,466,877 A | 11/1995 | Moore |
| 5,488,142 A | 1/1996 | Fall et al. |
| 5,571,870 A | 11/1996 | Bierschenk et al. |
| 5,578,278 A | 11/1996 | Fall et al. |
| 5,674,949 A | 10/1997 | Bierschenk et al. |
| 5,753,776 A | 5/1998 | Bierschenk et al. |
| 6,093,860 A | 7/2000 | Watanabe et al. |
| 6,255,536 B1 | 7/2001 | Worm et al. |
| 6,586,626 B1 | 7/2003 | Okazoe et al. |

FOREIGN PATENT DOCUMENTS

| | | |
|---|---|---|
| EP | 0 150 618 | 8/1985 |
| EP | 0 265 052 | 4/1988 |
| EP | 1 288 183 A1 | 3/2003 |
| EP | 1 323 703 A1 | 7/2003 |
| JP | 2-311438 | 12/1990 |
| JP | 10-116627 | 5/1998 |
| JP | 2001-139509 | 5/2001 |
| RU | 369112 | 11/1973 |
| RU | 2098403 | 12/1997 |
| WO | WO 95/25082 | 9/1995 |
| WO | WO 00/56694 | 9/2000 |
| WO | WO 01/46107 | 6/2001 |
| WO | WO 02/10107 | 2/2002 |

OTHER PUBLICATIONS

Okazoe et al, Journal of Fluorine Chemistry, A New Route to Perfluorinated Vinyl Ether Monomers: Synthesis of Perfluoro(alkoxyalkanoyl) Fluorides from Non-fluorinated Compounds, 2001, 112(1), pp. 109-116.*
K. Murata, et al., J. Am. Chem. Soc., vol. 120, No. 28, pp. 7117-7118, "The Thermal Decomposition of Perfluoroesters", 1998.
I. Tari, et al., J. Org. Chem., vol. 45, No. 7, pp. 1214-1217, "Synthesis of Halogenated Esters of Fluorinated Carboxylic Acids by the Regio- and Streospecfic Addition of Acyl Hypochlorites to Olefins", 1980.
English Abstracts of WO 01/16085, Mar. 8, 2001.
English Abstracts of WO 01/46093, Jun. 28, 2001.
English Abstracts of WO 01/94285, Dec. 13, 2001, abstract only.
English Abstracts of WO 01/04397, Jan. 17, 2002, abstract only.
English Abstract of WO 02/10106, Feb. 7, 2002, abstract only.
English Abstracts of WO 02/10108, Feb. 7, 2002, abstract only.
English Abstracts of WO 02/18314, Mar. 7, 2002, abstract only.
English Abstracts of WO 02/20445, Mar. 14, 2002, abstract only.
English Abstracts of WO 02/26679, Apr. 4, 2002, abstract only.

(Continued)

Primary Examiner—Paul A. Zucker
(74) Attorney, Agent, or Firm—Oblon, Spivak, McClelland, Maier & Neustadt, P.C.

(57) ABSTRACT

A process for producing a fluorinated ester through a small number of steps, is presented. The process for producing a fluorinated ester, comprises a transesterification step in which $R^{AF}$—$COOCF_2$—$R^{AF}$ and $R^A$—$CH_2OH$ are subjected to a transesterification reaction to obtain $R^{AF}$—$COOCH_2$—$R^A$, and a fluorination step in which the obtained compound is fluorinated to obtain a reaction product containing $R^{AF}$—$COOCF_2$—$R^{AF}$. Here, in the formulae, $R^A$ is a monovalent organic group, and $R^{AF}$ is the same group as $R^A$ or a monovalent organic group obtained by fluorination of $R^A$.

21 Claims, No Drawings

OTHER PUBLICATIONS

English Abstracts of WO 02/26682, Apr. 4, 2002, abstract only.
English Abstracts of WO 02/26686, Apr. 4, 2002, abstract only.
English Abstracts of WO 02/26687, Apr. 4, 2002, abstract only.
English Abstracts of WO 02/26688, Apr. 4, 2002, abstract only.
English Abstracts of WO 02/26689, Apr. 4, 2002, abstract only.
English Abstracts of WO 02/26693, Apr. 4, 2002, abstract only.
Patent Abstracts of Japan, JP 2000-351751, Dec. 19, 2000.
Derwent Publications, AN 2002-303929, XP-002322145, JP 2002-516241, Feb. 7, 2002.

* cited by examiner

PROCESS FOR PRODUCING A FLUORINATED ESTER, A FLUORINATED ACYL FLUORIDE AND A FLUORINATED VINYL ETHER

TECHNICAL FIELD

The present invention relates to a process for producing a fluorinated ester and a process for producing a fluorinated acyl fluoride and a fluorinated vinyl ether by using such a fluorinated ester.

BACKGROUND ART

A fluorinated ester is a compound useful as an intermediate for the synthesis of e.g. a fluorinated acyl fluoride or a fluorinated vinyl ether. The present applicants have proposed a series of processes, in which an esterification reaction, a fluorination reaction and a reaction to dissociate an ester bond, are combined, as a process for producing a fluorinated ester and a fluorinated acyl fluoride. They have also proposed a continuous process in which the fluorinated acyl fluoride produced by such a process is reused again for an esterification reaction (WO 00/56694).

Such a process is a process which essentially requires three steps i.e. the esterification step, the fluorination step and the step to dissociate an ester bond. Namely, it is a process in which the following fluorinated acyl fluoride (4) and the following compound (2) having a hydroxyl group, are subjected to an esterification reaction to obtain the following ester compound (3), which is fluorinated to obtain the following fluorinated ester (1), and the ester bond of the fluorinated ester (1) is dissociated to obtain a fluorinated acyl fluoride (4), which is used for the esterification reaction with the above compound (2) to carry out the same process (here, the meanings of symbols in the following formulae are the same as the meanings of the symbols mentioned hereinafter).

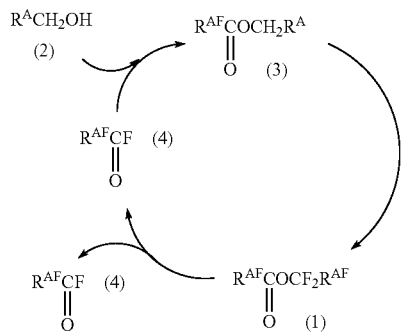

Further, as a process to obtain the fluorinated ester (1) more efficiently in a large amount, they have also proposed a process wherein a fluorinated diester having the same groups ($R^{AF}$) at both terminals of the molecule, is synthesized by an esterification reaction, and the two ester bonds of the diester are dissociated to obtain twice by mol of a fluorinated acyl fluoride.

It is an object of the present invention to provide a process whereby a fluorinated ester (1) and a fluorinated acyl fluoride (4) can be produced in large amounts efficiently through a smaller number of steps than the above-mentioned process. Another object of the present invention is to provide a process for producing a fluorinated vinyl ether by using the fluorinated ester (1) and the fluorinated acyl fluoride (4) obtained by such a process.

DISCLOSURE OF THE INVENTION

As a result of an extensive research to accomplish the above objects, the present inventors have found it possible to accomplish the above objects and to produce a fluorinated ester by mass production by combining a transesterification step of the fluorinated ester with a fluorination step. Further, they have found it possible to produce a fluorinated acyl fluoride or a fluorinated vinyl ether by using the fluorinated ester produced by such a process.

Namely, the present invention provides a process for producing the following fluorinated ester (1), which comprises a transesterification step in which the following fluorinated ester (1) and the following compound (2) are reacted for transesterification to obtain the following compound (3), and a fluorination step in which the compound (3) is then fluorinated to obtain the following fluorinated ester (1) in an amount larger than the molar amount prior to the transesterification:

$$R^{AF}\text{—COOCF}_2\text{—}R^{AF} \tag{1}$$

$$R^{AF}\text{—CH}_2\text{OH} \tag{2}$$

$$R^{AF}\text{—COOCH}_2\text{—}R^{A} \tag{3}$$

wherein $R^{A}$ is a monovalent organic group, and $R^{AF}$ is the same group as $R^{A}$ or a monovalent organic group obtained by fluorination of $R^{A}$.

Further, the present invention provides the above process for producing the fluorinated ester (1) wherein in the fluorination step, the fluorination of the compound (3) is carried out by introducing fluorine gas into a liquid phase.

Further, the present invention provides the above process for producing the fluorinated ester (1), wherein in the fluorination step, the compound (3) containing the following fluorinated acyl fluoride (4) and/or the compound (1) formed in the transesterification step, is used as it contains the fluorinated acyl fluoride (4) and/or the compound (1):

$$R^{AF}\text{—COF} \tag{4}$$

wherein $R^{AF}$ is as defined above.

Further, the present invention provides the above-mentioned process for producing the fluorinated ester (1), wherein the transesterification step is carried out in the absence of a solvent.

Further, the present invention provides the above process for producing the fluorinated ester (1), wherein the fluorinated ester (1) in the transesterification step is the fluorinated ester (1) obtained in the fluorination step.

Further, the present invention provides the above process for producing the fluorinated ester (1), which includes a step of obtaining the following fluorinated ester (1) by fluorinating in a liquid phase the following compound (3) obtained by reacting the following fluorinated acyl fluoride (4) and the following compound (2), and wherein the fluorinated ester (1) obtained in said step is used as the fluorinated ester (1) in the transesterification step:

$$R^{AF}\text{—COF} \tag{4}$$

$$R^{A}\text{—CH}_2\text{OH} \tag{2}$$

$$R^{AF}\text{—COOCH}_2\text{—}R^{A} \tag{3}$$

$$R^{AF}\text{—COOCF}_2\text{—}R^{AF} \tag{1}$$

wherein $R^{A}$ and $R^{AF}$ are as defined above.

Further, the present invention provides a process for producing a fluorinated acyl fluoride (4), which comprises dissociating the ester bond of the following fluorinated ester (1) obtained by the above process:

$$R^{AF}-COOCF_2-R^{AF} \quad (1)$$

$$R^{AF}-COF \quad (4)$$

wherein $R^{AF}$ is as defined above.

Further, the present invention provides the above process for producing the fluorinated ester (1), wherein the fluorinated ester (1) is the following compound (1a), the compound (2) is the following compound (2a), the compound (3) is the following compound (3a), and $R^{AF}$ is $R^{AF1}O-CF(CF_3)-$:

$$R^{AF1}O-CF(CF_3)-COOCF_2-CF(CF_3)-OR^{AF1} \quad (1a)$$

$$R^{A1}O-CX^1(CX^2X^3X^4)-CH_2OH \quad (2a)$$

$$R^{AF1}O-CF(CF_3)-COOCH_2-CX^1(CX^2X^3X^4)-OR^{A1} \quad (3a)$$

wherein $R^{A1}$ is a monovalent organic group, $R^{AF1}$ is the same group as said $R^{A1}$ or a monovalent organic group obtained by fluorination of said $R^{A1}$, and each of $X^1, X^2, X^3$ and $X^4$ which may be the same or different, is a hydrogen atom or a fluorine atom.

Further, the present invention provides a process for producing the following fluorinated vinyl ether (5a), which comprises dissociating the ester bond of the following compound (1a) obtained by the above process, to obtain the following compound (4a), and pyrolyzing the compound (4a):

$$R^{AF1}O-CF(CF_3)-COOCF_2-CF(CF_3)-OR^{AF1} \quad (1a)$$

$$R^{AF1}O-CF(CF_3)-COF \quad (4a)$$

$$R^{AF1}O-CF=CF_2 \quad (5a)$$

wherein $R^{AF1}$ is as defined above.

Further, the present invention provides a process for producing the following fluorinated vinyl ether (5a), which comprises pyrolyzing the following compound (1a) obtained by the above process, at a temperature of at least 250° C.:

$$R^{AF1}O-CF(CF_3)-COOCF_2-CF(CF_3)-OR^{AF1} \quad (1a)$$

$$R^{AF1}O-CF=CF_2 \quad (5a)$$

wherein $R^{AF1}$ is as defined above.

BEST MODE FOR CARRYING OUT THE INVENTION

A typical transesterification reaction in which at most twice by mol of the compound (2) is reacted to the fluorinated ester (1) for transesterification, is represented by the following formulae, wherein $R^A$ and $R^{AF}$ are as defined above.

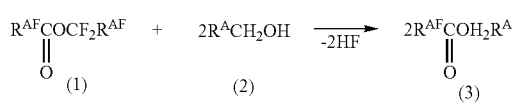

The mechanism for the transesterification reaction is considered to be such that firstly, an equimolar amount of the compound (2) is reacted to the fluorinated ester (1) for transesterification to form an equimolar amount of the compound (3) and an equimolar amount of the fluorinated acyl fluoride (4) ($R^{AF}COF$), and then, the fluorinated acyl fluoride (4) is further reacted with an equimolar amount of the compound (2) to form an equimolar amount of the compound (3). Namely, twice by mol of the compound (2) is reacted to the fluorinated ester (1) to form twice by mol of the compound (3). Then, twice by mol of the compound (3) formed by the transesterification reaction, is fluorinated to form twice by mol of the fluorinated ester (1).

This series of reactions will be shown by the following formulae. Namely, the transesterification reaction and then the fluorination reaction are carried out, by using twice by mol of the compound (2) relative to the fluorinated ester (1), whereby theoretically, the fluorinated ester (1) will increase to twice by mol (Here, $R^A$ and $R^{AF}$ in the formulae are as defined above.).

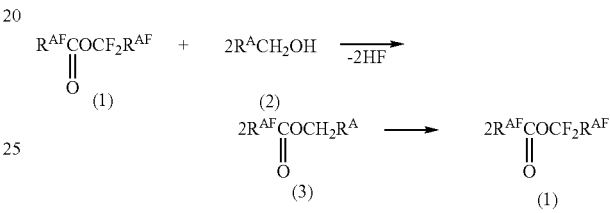

Now, the present invention will be described with reference to this reaction mechanism.

In the compounds of the present invention, each of $R^A$ and $R^{A1}$ is a monovalent organic group. In the present invention, "an organic group" means a group containing at least one carbon atom, and the organic group may have any one of a straight chain structure, a branched structure or a cyclic structure.

As $R^A$ and $R^{A1}$, a $C_{1-20}$ monovalent organic group is preferred. As the monovalent organic group, a monovalent hydrocarbon group, a halogeno monovalent hydrocarbon group, a heteroatom-containing monovalent hydrocarbon group or a halogeno (heteroatom-containing monovalent hydrocarbon) group is preferred. As the monovalent hydrocarbon group among such groups, a monovalent aliphatic hydrocarbon group is preferred. In the monovalent aliphatic hydrocarbon group, an unsaturated bond may be present. As the monovalent organic group, a monovalent saturated hydrocarbon group, a partially halogeno monovalent saturated hydrocarbon group, an etheric oxygen atom-containing monovalent hydrocarbon group or a partially halogeno (etheric oxygen atom-containing monovalent saturated hydrocarbon) group is more preferred. Here, a "saturated" group is a group wherein carbon—carbon bonds are made solely of single bonds, and a "hetero atom-containing" group means a group containing a hetero atom such as an oxygen atom, a nitrogen atom or a sulfur atom, in the group. As the hetero atom, an etheric oxygen atom (—O—) or =O is, for example, preferred. Among them, an etheric oxygen atom is particularly preferred.

The monovalent saturated hydrocarbon group may be an alkyl group, a cycloalkyl group or a cycloalkylalkyl group. The cycloalkyl group is preferably a cycloalkyl group of a 3- to 6-membered ring, or a group having at least one hydrogen atom of such a cycloalkyl group substituted by an alkyl group. The cycloalkylalkyl group is preferably a group having one hydrogen atom of a $C_{1-3}$ alkyl group substituted by the above cycloalkyl group.

The halogeno monovalent saturated hydrocarbon group may be a group having at least one hydrogen atom of the above monovalent saturated hydrocarbon group halogenated, and it is preferably a fluoroalkyl group or a fluoro (partially chloroalkyl) group. As the etheric oxygen atom-containing monovalent saturated hydrocarbon group, an alkoxyalkyl group or an alkoxy group is particularly preferred.

The halogeno (etheric oxygen atom-containing monovalent saturated hydrocarbon) group may be a group having at least one hydrogen atom of the above etheric oxygen atom-containing monovalent saturated hydrocarbon group halogenated, and it is preferably a fluoroalkoxy group, a fluoroalkoxyalkyl group, a chloroalkoxy group, a chloroalkoxyalkyl group, a fluoro (partially chloroalkoxy) group or a fluoro (partially chloroalkoxyalkyl) group.

From the availability of the compound (2) and economical efficiency, each of $R^A$ and $R^{A1}$ is preferably a monovalent organic group containing no fluorine atom, which can be fluorinated by a reaction with fluorine in a liquid phase. As such a group, an alkyl group, an alkoxy group, an alkoxyalkyl group, a partially chloroalkyl group, a partially chloroalkoxy group or a partially chloroalkoxyalkyl group is particularly preferred.

In the above compounds, $R^{AF}$ is the same group as $R^A$ or a monovalent organic group obtained by fluorination of $R^A$, and $R^{AF1}$ is the same group as $R^{A1}$ or a monovalent organic group obtained by fluorination of $R^{A1}$. In the present invention, "fluorination" is a reaction to introduce a fluorine atom. The fluorination in the present invention is usually a reaction to substitute a fluorine atom for a hydrogen atom bonded to a carbon atom. However, in a case where a carbon—carbon unsaturated double bond (—CH=CH—) is present, a reaction to substitute a fluorine atom for a hydrogen atom and an addition reaction will take place. In a case where $R^A$ and $R^{A1}$ are groups which can not be fluorinated, or they are groups which can be fluorinated, but are not fluorinated, $R^{AF}$ and $R^{AF1}$ are the same groups as $R^A$ and $R^{A1}$, respectively. For example, in a case where $R^A$ and $R^{A1}$ are perhalogeno monovalent saturated hydrocarbon groups or perhalogeno (etheric oxygen atom-containing monovalent saturated hydrocarbon) groups, the halogen atoms in these groups will not change even when reacted with fluorine in a liquid phase, and accordingly, $R^{AF}$ and $R^{AF1}$ will be the same groups as the above $R^A$ and $R^{A1}$, respectively.

Each of $R^{AF}$ and $R^{AF1}$ is preferably a group which will not change even by a fluorination reaction, since the aftermentioned continuous process can thereby be carried out. As such a group, a perfluoromonovalent organic group is preferred, a perfluoromonovalent saturated hydrocarbon groups; a perfluoro (partially chloromonovalent saturated hydrocarbon) group, a perfluoro (etheric oxygen atom-containing monovalent saturated hydrocarbon) group or a perfluoro [partially halogeno (etheric oxygen atom-containing monovalent saturated hydrocarbon) group; is particularly preferred, and a perfluoroalkyl group, a perfluoro (partially chloralkyl) group, a perfluoroalkoxy group, a perfluoro (partially chloroalkoxy) group, a perfluoroalkoxyalkyl group or a perfluoro (partially chloroalkoxyalkyl) group is especially preferred.

Each of $X^1$ to $X^4$ in the compound (2a) and the compound (3a) is a hydrogen atom or a fluorine atom. In view of the availability of the compound (2a), it is preferred that all of $X^1$ to $X^4$ are hydrogen atoms.

In this specification, a "halogeno" group means a group having at least one of hydrogen atoms bonded to carbon atoms substituted by a halogen atom; a "perhalogeno" group means a group having substantially all hydrogen atoms bonded to carbon atoms substituted by halogen atoms; and a "partially halogeno" group means a group having some of hydrogen atoms bonded to carbon atoms substituted by halogen atoms. In a case where the halogen atoms are fluorine atoms, such groups may be represented by "perfluoro", "partially fluoro" or the like. Further, the "perhalogeno" group and the "partially halogeno" group may contain halogen atoms of one type or of two or more different types. The "perhalogeno" group is preferably a group having all hydrogen atoms bonded to carbon atoms substituted by halogen atoms, but even in a case where non-substituted hydrogen atoms still remain, so long as the nature as a group is substantially equal to a "perhalogeno" group, such group will be included in the concept of the "perhalogeno" group.

Compounds of the following formulae may be mentioned as specific examples of the fluorinated ester (1) and the compound (1a).

$CF_3CF_2CF_2OCF(CF_3)CF_2OCF(CF_3)CF_2OCOCF(CF_3)$ $OCF_2CF(CF_3)$—$OCF_2CF_2CF_3$,
$CF_3(CF_2)_kOCF(CF_3)CF_2OCOCF(CF_3)O(CF_2)_kCF_3$
(wherein k is an integer of from 0 to 9.).

Compounds of the following formulae may be mentioned as specific examples of the compound (2) and the compound (2a).

$CH_3CH_2CH_2OCH(CH_3)CH_2OCH(CH_3)CH_2OH$,
$CH_3(CH_2)_kOCH(CH_3)CH_2OH$ (wherein k is an integer of from 0 to 9.).

Compounds of the following formulae may be mentioned as specific examples of the compound (3) and the compound (3a).

$CH_3CH_2CH_2OCH(CH_3)CH_2OCH(CH_3)CH_2OCOCF(CF_3)$ $OCF_2CF(CF_3)$—$OCF_2CF_2CF_3$,
$CH_3(CH_2)_kOCH(CH_3)CH_2OCOCF(CF_3)O(CF_2)_kCF_3$
(wherein k is an integer of from 0 to 9.).

Compounds of the following formulae may be mentioned as specific examples of the fluorinated acyl fluoride (4) and the compound (4a).

$CF_3CF_2CF_2OCF(CF_3)CF_2OCF(CF_3)COF$,
$CF_3(CF_2)_kOCF(CF_3)COF$ (wherein k is an integer of from 0 to 9.)

Compounds of the following formulae may be mentioned as specific example of the fluorinated vinyl ether (5a).

$CF_3CF_2CF_2OCF(CF_3)CF_2OCF=CF_2$,
$CF_3(CF_2)_kOCF=CF_2$ (wherein k is an integer of from 0 to 9.).

The transesterification step in the present invention is a step in which the fluorinated ester (1) and the compound (2) are reacted for transesterification to obtain the compound (3).

In the transesterification step, the proportion (the molar ratio) of the compound (2) to be reacted to the fluorinated ester (1) is not particularly limited and may be any optional molar ratio. However, if the molar ratio of the compound (2) exceeds twice by mol, an unreacted compound (2) will remain in the product of the transesterification reaction. And the presence of the unreacted compound (2) is likely to cause an undesirable reaction in the fluorination step. Therefore, it will be required to separate such an unreacted compound (2) prior to the subsequent fluorination step. Further, even if the compound (2) is reacted in an amount exceeding twice by mol, it is stoichiometrically impossible to obtain more than twice by mol of the compound (3) relative to the fluorinated ester (1). Accordingly, the proportion of the compound (2) to be reacted to the fluorinated ester (1) is preferably at most twice by mol to the fluorinated ester (1).

On the other hand, if the molar ratio of the compound (2) to be reacted to the fluorinated ester (1) is too small, the amount of the compound (3) to be formed, will decrease. Further, the fluorinated acyl fluoride (4) as a reaction intermediate and/or an unreacted fluorinated ester (1) will be included in the product. Further, if the proportion of the compound (2) is not higher than once by mol, it is impossible to accomplish the purpose of producing the fluorinated acyl fluoride (1) by mass production. From the foregoing, the proportion of the compound (2) to be reacted to the fluorinated ester (1) is preferably from once by mol to twice by mol, more preferably from 1.5 times by mol to twice by mol, especially preferably twice by mol, to the fluorinated ester (1).

The fluorinated ester (1), the compound (2) and the compound (3) to be used in the transesterification step are preferably the compound (1a), the compound (2a) and the compound (3a), respectively.

The transesterification reaction of the fluorinated ester (1) and the compound (2) can be carried out under known reaction conditions. Said reaction may be carried out in the presence of a solvent (hereinafter referred to as "solvent 1"). However, it is preferred to carry out the reaction in the absence of solvent 1, since it is thereby possible to use the crude liquid as it is in the next fluorination step. When solvent 1 is to be used, it is preferably dichloromethane, chloroform, triethylamine or a mixed solvent of triethylamine and tetrahydrofuran. The amount of solvent 1 to be used, is preferably from 50 to 500 mass %, based on the total amount of the fluorinated ester (1) and the compound (2).

In the reaction of the fluorinated ester (1) and the compound (2), HF will be generated. As a HF scavenger, an alkali metal fluoride (NaF or KF is preferred) or a trialkylamine may, for example, be incorporated in the reaction system. However, it is preferred that in the absence of such a HF scavenger, HF is discharged out of the reaction system as carried by a nitrogen stream, since it is thereby possible to use the crude liquid as it is in the next fluorination step. In a case where an alkali metal fluoride is to be employed, its amount is preferably from 1 to 10 times by mol to the fluorinated ester (1).

The temperature for the reaction of the fluorinated ester (1) and the compound (2) is preferably at least −50° C. and preferably at most +100° C. or at most the boiling point of the solvent, in a usual case. In a case where in the absence of a HF scavenger, HF is discharged out of the reaction system as carried by a nitrogen stream, the reaction temperature is preferably at least +20° C. and at most +100° C. or at most the boiling point of the solvent. Further, the reaction time for the reaction may suitably be changed depending upon the supply rate of the feed materials and the amounts of the compounds to be used for the reaction. The reaction pressure (the gauge pressure, the same applies hereinafter) is preferably from atmospheric pressure to 2 MPa.

The composition of compounds contained in the reaction product of the transesterification step may optionally be changed depending upon the amounts of the compounds consumed by the reaction or the reactivities of the compounds. Namely, the reaction product in the transesterification step may contain, in addition to the compound (3), unreacted fluorinated ester (1) and compound (2), and a fluorinated acyl fluoride (4) which may be present as a reaction intermediate. Among them, if the compound (2) is contained in the reaction product, it should better be removed. On the other hand, the presence of the fluorinated acyl fluoride (4) in the reaction product will present no adverse effect in the fluorination step subsequent to the transesterification step, and it is rather preferred not to remove it, since it can be a liquid phase in the fluorination step. Here, in a case where the fluorination step is carried out while the reaction system contains the fluorinated acyl fluoride (4), the fluorinated acyl fluoride (4) will likely be present also in the reaction product of the fluorination step. However, if the after-mentioned continuous process is carried out in the presence of the fluorinated acyl fluoride (4), the compound (2) and the fluorinated acyl fluoride (4) will be reacted in the transesterification step in the second cycle to form the compound (3). Further, in a case where an unreacted fluorinated ester (1) is present in the reaction crude product in the transesterification step, it is preferred not to remove such a fluorinated ester (1), since it can be a liquid phase in the fluorination step. Namely, in a case where the reaction product in the transesterification step contains, in addition to the compound (3), the fluorinated acyl fluoride (4) or the fluorinated ester (1), it may be used as it is in the fluorination step.

In the present invention, the fluorine content of the compound (3) is preferably at least 30 mass %, whereby liquid phase fluorination being an advantageous fluorination method, can readily be carried out. If the fluorine content of the compound (3) is less than 30 mass %, the solubility in the liquid phase tends to be inadequate in the liquid phase fluorination method. The fluorine content of the compound (3) can be optionally adjusted depending upon the type of the liquid phase, but the fluorine content is more preferably from 30 to 86 mass %, still more preferably from 30 to 76 mass %.

Further, the molecular weight of the compound (3) is preferably from 200 to 1000. If the molecular weight of the compound (3) is less than 200, the boiling point of the compound (3) tends to be low, whereby in the fluorination process, the compound (3) is likely to evaporate, and the yield of the fluorinated product tends to decrease. Further, a decomposition reaction is likely to take place. On the other hand, if the molecular weight exceeds 1000, the solubility in the liquid phase is likely to decrease when the liquid phase fluorination method is to be carried out, or purification tends to be difficult.

The compound (3) obtained in the above transesterification step will be fluorinated in the fluorination step to form a fluorinated ester (1). The fluorinated ester (1) may be a compound having the compound (3) partially fluorinated. However, the fluorinated ester (1) is preferably a compound having the compound (3) completely fluorinated, since it is difficult to control the positions for introduction of fluorine atoms in the fluorination reaction and since the process of the present invention can thereby be carried out by a continuous process which will be described hereinafter. However, in a case where an unreacted compound (3) and a partially fluorinated compound (3) are contained in the product of the fluorination step, the continuous process may be carried out as they are contained, whereby the ratio of fluorine introduced to the compound (3) can be increased.

From the viewpoint of the yield and the operation efficiency of the reaction, the fluorination reaction in the fluorination step is preferably carried out in a liquid phase. The fluorination reaction may be carried out by an ECF method, a cobalt fluorination method or a method of fluorinating in a gas phase. However, from the viewpoint of the reaction yield and the reaction operation efficiency, a liquid phase fluorination method wherein fluorination is carried out in a liquid phase, is a remarkably advantageous method and thus is preferred.

The liquid phase fluorination method is preferably carried out by introducing fluorine gas in the liquid phase wherein the compound (3) is present. In such a case, fluorine gas may be used as it is, or a fluorine gas diluted by an inert gas may be employed. As the inert gas, nitrogen gas or helium gas is preferred, and from the economical reason, nitrogen gas is particularly preferred. The amount of fluorine in nitrogen gas is not particularly limited, and it is preferably at least 10 vol %, from the viewpoint of the efficiency, and particularly preferably at least 20 vol %.

The liquid phase is preferably formed by a solvent which essentially contains a C—F bond without containing a C—H bond. As such a solvent (hereinafter referred to as "solvent 2"), it is preferred to employ a solvent which is capable of dissolving at least 1 mass % of the compound (3), particularly a solvent which is capable of dissolving at least 5 mass % thereof. Further, solvent 2 is preferably a fluorinated ester (1) or a fluorinated acyl fluoride (4) as a product in the fluorination step. In a case where the fluorinated ester (1) is used as solvent 2, there is a merit in that post treatment after the reaction is easy. Further, in a case where the fluorinated acyl fluoride (4) is used as the solvent for the reaction, and in a case where the after-mentioned pyrolysis step is to be carried out, such step can be carried out without separating the fluorinated acyl fluoride (4) from the product in the fluorination step.

In a case where a solvent other than the fluorinated ester (1) and the fluorinated acyl fluoride (4) is used as solvent 2, it may, for example, be a perfluoroalkane, a perfluoroether, a perfluoropolyether, a chlorofluorocarbon, a chlorofluoropolyether, a perfluoroalkylamine or an inert fluid. The amount of solvent 2 is preferably at least 5 times by mass, particularly preferably from 10 to 100 times by mass, relative to the compound (3).

As the reaction system for the fluorination reaction, a batch system or a continuous system may be mentioned. As the continuous system, the following continuous system 1 or continuous system 2 may be mentioned. However, from the viewpoint of the reaction yield and selectivity, continuous system 2 is preferred. Further, fluorine gas may be used as diluted with an inert gas such as nitrogen gas in either case where the fluorination is carried out in a batch system or in a continuous system. In the following description, fluorine gas may be a diluted fluorine gas.

Continuous System 1

A method in which the compound (3) and solvent 2 are charged into a reactor, stirring is initiated, and after controlling the temperature and pressure to the predetermined reaction temperature and reaction pressure, fluorine gas, or fluorine gas and solvent 2, are continuously supplied to carry out the reaction.

Continuous System 2

A method in which solvent 2 is charged into a reactor, stirring is initiated, and after adjusting the temperature and pressure to the prescribed reaction temperature and reaction pressure, the compound (3) and fluorine gas are continuously and simultaneously supplied in a prescribed molar ratio.

When the compound (3) is supplied in continuous system 2, it is preferred to supply the compound (3) diluted with solvent 2, whereby the selectivity can be improved, and the amount of byproducts can be suppressed. Further, when the compound (3) is diluted with the solvent in continuous system 2, the amount of solvent 2 to the compound (3) is made preferably to be at least 5 times by mass, particularly preferably to be at least 10 times by mass. Such a condition is the same also in a case where the compound (3a) is used in continuous system 2.

With respect to the amount of fluorine to be used for the fluorination reaction, in either case where the reaction is carried out in a batch system or in a continuous system, it is preferred that fluorine gas is present so that the amount of fluorine will be always in an excess equivalent to hydrogen atoms to be fluorinated, and it is particularly preferred that fluorine gas is used so that it will be at least 1.5 times by equivalent (i.e. at least 1.5 times by mol) from the viewpoint of the selectivity.

The reaction temperature for the fluorination reaction is usually preferably at least −60° C. and at most the boiling point of the compound (3), and from the viewpoint of the reaction yield, selectivity and industrial applicability, it is particularly preferably from −50° C. to +100° C., further preferably from −20° C. to +50° C. The reaction pressure for the fluorination reaction is not particularly limited, and a pressure from atmospheric pressure to 2 MPa is particularly preferred from the viewpoint of the reaction yield, selectivity and industrial applicability.

Further, in order to let the fluorination reaction proceed efficiently, it is preferred to add a C—H bond-containing compound into the reaction system or to carry out ultraviolet irradiation at a later stage of the reaction. For example, in a batch system reaction, it is preferred to add a C—H bond-containing compound into the reaction system or to carry out ultraviolet irradiation at a later stage of the fluorination reaction. In a continuous system reaction, it is preferred to supply a C—H bond-containing compound or to irradiate ultraviolet rays while continuing the supply of fluorine gas, upon completion of the introduction of the compound (3). It is thereby possible to efficiently fluorinate the compound (3) present in the reaction system, whereby the reaction rate can remarkably be improved.

As the C—H bond-containing compound, an aromatic hydrocarbon is preferred, and benzene or toluene may, for example, be particularly preferred. The amount of the CH bond-containing compound is preferably from 0.1 to 10 mol %, particularly preferably from 0.1 to 5 mol %, based on hydrogen atoms in the compound (3).

The C—H bond-containing compound is added in such a state that fluorine gas is present in the reaction system. Further, in a case where the C—H bond-containing compound is added, it is preferred to pressurize the reaction system. The pressure for pressurizing is preferably from 0.01 to 5 MPa.

In the fluorination step, if a reaction to substitute fluorine atoms for hydrogen atoms occurs, HF will be formed as a byproduct. To remove the byproduct HF, it is preferred to incorporate a scavenger for HF in the reaction system, or to contact the HF scavenger with the outlet gas at the gas outlet of the reactor. As such a HF scavenger, the same one as mentioned above may be employed, and NaF is preferred.

In a case where a HF scavenger is permitted to coexist in the reaction system, its amount is preferably from 1 to 20 times by mol, particularly preferably from 1 to 5 times by mol, to the total amount of hydrogen atoms present in the compound (3). In a case where the HF scavenger is placed at the gas outlet of the reactor, it is advisable to arrange (a) a cooler (preferably to maintain the temperature at from 10° C. to room temperature, particularly preferably at about 20° C.), (b) a packed layer of NaF pellets and (c) a cooler (preferably to maintain the temperature from −78° C. to +10° C., preferably from −30° C. to 0° C.) in series in the order of (a)-(b)-(c). Further, a liquid returning line to return the condensed liquid from the cooler (c) to the reactor, may be provided.

The crude product containing the fluorinated ester (1) obtained in the fluorination step, may be used as it is depending upon the particular purpose or may be purified to have a high purity. As a purification method, a method of distilling the crude product as it is under atmospheric pressure or reduced pressure, may, for example, be mentioned.

In the process for producing the fluorinated ester (1) of the present invention, by carrying out the transesterification step and the fluorination step once by using 1 mol of the fluorinated ester (1), the maximum of 2 mols of the fluorinated ester (1) can be obtained. Further, by carrying out the same steps starting from the obtained 2 mols of the fluorinated ester (1), the maximum of 4 mols of the fluorinated ester (1) can be obtained. Namely, by repeating the transesterification step and the fluorination step n times, the maximum of $2^n$ times by mol of the fluorinated ester (1) can be obtained. Thus, by repeating the same steps by using the fluorinated ester (1) obtained by the transesterification step and the fluorination step until the desired amount is obtained, the fluorinated ester (1) can be continuously and efficiency produced by mass production. This reaction scheme may be represented by the following chemical formulae.

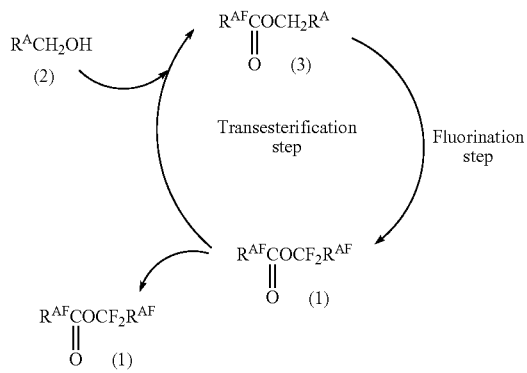

In the present invention, the fluorinated ester (1) produced by carrying out the transesterification step and the fluorination step only once, may be recovered, or the fluorinated ester (1) may be recovered after carrying out the transesterification step and the fluorination step plural times.

The fluorinated ester (1) may be used as it is for the particular purpose or may be converted to another compound. For example, the fluorinated ester (1) may be subjected to an ester dissociation reaction, whereby a fluorinated acyl fluoride (4) may be formed stoichiometrically twice by mol to the fluorinated ester (1).

According to the process for producing a fluorinated ester of the present invention, the fluorinated acyl fluoride (4) can be produced in a smaller number of steps than the process disclosed in WO 00/56694. Further, it is advantageous that the temperature condition in the transesterification step of the present invention is usually a lower temperature than the temperature condition for the esterification step in a conventional method.

The fluorinated ester (1) as the starting material in the process of the present invention, is a compound having the same groups ($R^{AF}$) at both terminals of the molecule. This fluorinated ester (1) is preferably synthesized by a method disclosed in e.g. WO 00/56694.

Namely, the fluorinated ester (1) is preferably obtained by fluorinating in a liquid phase a compound (3) which is obtained by reacting the fluorinated acyl fluoride (4) and the compound (2). The reaction of the fluorinated acyl fluoride (4) and the compound (2), may be carried out in the presence of a solvent. However, it is preferred to carry out it in the absence of a solvent, from the viewpoint of the volume efficiency.

In the reaction of the compound (2) and the fluorinated acyl fluoride (4), HF will be formed. Accordingly, a HF scavenger may be incorporated in a reaction system, or without using a HF scavenger, HF may be discharged out of the reaction system as carried by a nitrogen stream. As the HF scavenger, the same one as mentioned above can be used. The reaction temperature of the compound (2) and the fluorinated acyl fluoride (4) is preferably at least $-50°$ C. and preferably at most $+100°$ C. or at most the boiling point of the solvent. Further, the reaction time for the reaction may suitably be changed depending upon the supply rate of the starting materials and the amounts of the compounds to be used for the reaction. The reaction pressure is preferably from atmospheric pressure to 2 MPa.

The crude product containing the compound (3), formed by the reaction of the compound (2) and the fluorinated acyl fluoride (4), may be purified depending upon the particular purpose, or may be used as it is for the next reaction, etc. In a case where the crude product contains an unreacted compound (2), it is advisable to remove it by purification with a view to letting the fluorination reaction proceed smoothly. As a purification method for such crude product, a method of distilling the crude product as it is, a method of treating the crude product with a dilute aqueous alkaline solution, followed by liquid separation, a method of extracting the crude product with a suitable organic solvent, followed by distillation, or silica gel column chromatography, may, for example, be mentioned.

After thus obtaining the compound (3) from the compound (2) and the fluorinated acyl fluoride (4), the compound (3) is fluorinated in a liquid phase to obtain a fluorinated ester (1). With respect to the fluorination reaction conditions in this case, the fluorination can be carried out in the same manner as in the fluorination step in the above-mentioned process for producing a fluorinated ester.

From the fluorinated ester (1) obtainable by the process of the present invention as described above, it is possible to further produce a fluorinated acyl fluoride (4) and a fluorinated vinyl ether (5a).

As a method for producing a fluorinated acyl fluoride (4) from the fluorinated ester (1), a dissociation reaction of an ester bond as disclosed in WO 00/56694, may be mentioned. The dissociation reaction of the ester bond is a reaction shown by the following formulae, whereby theoretically, from 1 mol of the fluorinated ester (1), 2 mols of the fluorinated acyl fluoride (4) can be obtained.

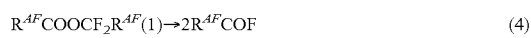

In a case where the dissociation reaction of the ester bond is to be carried out in a liquid phase method, it may be carried out in the absence of a solvent or in the presence of a solvent (hereinafter referred to as "solvent 3"). As a specific example of solvent 3, an inert solvent such as perfluorotrialkylamine or perfluorodecalin, or chlorotrifluoroethylene oligomer having a high boiling point among chlorofluorocarbons, is preferred. Further, the amount of solvent 3 is preferably from 10 to 1000 mass %, to the fluorinated ester (1).

As a method for producing the fluorinated vinyl ether (5a) from the compound (1a) being the fluorinated ester (1), a method of obtaining the fluorinated vinyl ether (5a) from the compound (1a) via the following compound (4a) (hereinafter referred to as "pyrolysis step-1"), or a method of obtaining the fluorinated vinyl ether (5a) directly from the compound (1a) (hereinafter referred to as "pyrolysis step-2").

As shown by the following formulae, the pyrolysis step-1 is a step for producing the fluorinated vinyl ether (5a) by carrying out a dissociation step of the ester bond to obtain the compound (4a) by dissociating the ester bond of the compound (1a) and a step of pyrolyzing the compound (4a). The pyrolysis step-2 is a step for obtaining the fluorinated vinyl ether (5a) by directly pyrolyzing the compound (1a) at a temperature of at least 250° C.

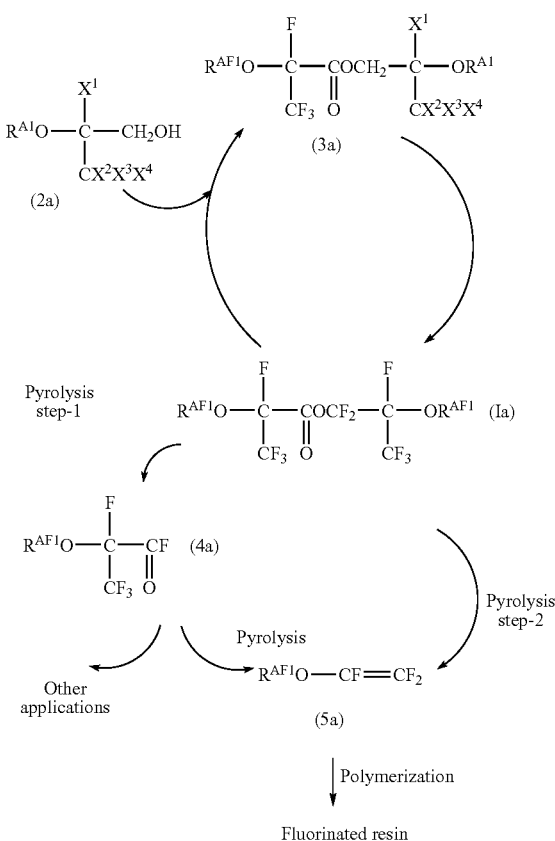

The pyrolysis step-1 can be carried out under the same conditions as the above-described conditions for the pyrolysis of the ester bond of the fluorinated ester (1), whereby theoretically, from 1 mol of the fluorinated ester (1a), 2 mols of the compound (4a) can be obtained. Further, the step of pyrolyzing the compound (4a) can be carried out, for example, by a gas phase pyrolysis of the compound (4a) or a pyrolysis of an alkali metal salt of a carboxylic acid obtained by reacting the compound (4a) and an alkali metal hydroxide.

The reaction temperature for the gas phase pyrolysis of the compound (4a) is preferably from 250 to 400° C., more preferably from 250 to 350° C. Whereas, the reaction temperature for the pyrolysis of the above alkali metal salt of a carboxylic acid, is preferably from 150 to 350° C., more preferably from 200 to 280° C. If the reaction temperature for the gas phase pyrolysis is less than 250° C., or if the reaction temperature for the pyrolysis of the alkali metal salt of a carboxylic acid is less than 150° C., the conversion to the fluorinated vinyl ether (5a) tends to be low. On the other hand, if the reaction temperature for the gas phase pyrolysis exceeds 400° C., or if the reaction temperature for the pyrolysis of the alkali metal salt of a carboxylic acid exceeds 350° C., pyrolysates other than the fluorinated vinyl ether (5a) tend to increase as pyrolysates obtainable from the compound (4a).

It is preferred to carry out the gas phase pyrolysis of the compound (4a) by a continuous reaction. The continuous reaction is preferably carried out by a method in which a vaporized compound (4a) is passed through the heated reaction tube to obtain the formed fluorinated vinyl ether (5a) as an outlet gas, and this outlet gas is condensed and continuously recovered. In a case where the pyrolysis is carried out by a gas phase reaction, it is preferred to employ a tubular reactor. In a case where a tubular reactor is employed, the retention time is preferably from about 0.1 second to 10 minutes by superficial velocity basis. The reaction pressure is not particularly limited. Further, in a case where the compound (4a) is a high boiling point compound, it is preferred to carry out the reaction under reduced pressure. Especially when the compound (4a) is a low boiling point compound, it is preferred to carry out the reaction under an elevated pressure, whereby decomposition of the product can be suppressed and the reaction rate can be increased.

In a case where the gas phase pyrolysis is carried out by means of a tubular reactor, it is preferred to pack glass, an alkali metal salt or an alkaline earth metal salt in the reaction tube for the purpose of accelerating the reaction. As such an alkali metal salt or an alkaline earth metal salt, a carbonate or a fluoride is preferred. As the glass, a common soda glass may be mentioned, and glass beads are particularly preferred, whereby flowability is improved in the form of beads. The alkali metal salt may, for example, be sodium carbonate, sodium fluoride, potassium carbonate or lithium carbonate. The alkaline earth metal salt may, for example, be calcium carbonate, calcium fluoride or magnesium carbonate. Further, in a case where glass, an alkali metal salt or an alkaline earth metal salt is to be packed in the reaction tube, it is particularly preferred to employ glass beads or light ash of sodium carbonate, having a particle size of from about 100 to 250 μm, whereby a fluidized bed type reaction system can be employed.

In the gas phase pyrolysis, it is preferred to carry out the reaction in the presence of an inert gas which will not be involved directly in the pyrolysis, for the purpose of accelerating the vaporization of the compound (4a). As such an inert gas, nitrogen, carbon dioxide, helium or argon may, for example, be mentioned.

The amount of the inert gas is preferably from about 0.01 to 50 vol %, based on the compound (4a). If the amount of the inert gas is too much, the recovery of the product is likely to be low, such being undesirable. On the other hand, if the boiling point of the compound (4a) is high, the pyrolysis may be carried out by a liquid phase reaction.

The pyrolysis step-2 can be carried out by a gas phase pyrolysis or a liquid phase pyrolysis. In a case where the boiling point of the compound (1a) under atmospheric pressure is from 50° C. to 350° C., it is preferred to employ a gas phase pyrolysis. However, the temperature for the pyrolysis is required to be at least 250° C., preferably from 250 to 450° C., in either gas phase or liquid phase pyrolysis. If the temperature for the pyrolysis exceeds 450° C., the fluorinated vinyl ether (5a) as the product of the pyrolysis, will further undergo pyrolysis, whereby the yield tends to be low.

In a case where the pyrolysis step-2 is carried out by a gas phase reaction, it is preferred to carry out the reaction by means of a tubular reactor in the same manner as for the gas phase pyrolysis of the compound (4a). In a case where the compound (1a) is a high boiling point compound, it is preferred to carry out the pyrolysis under reduced pressure. In a case where it is a low boiling point compound, it is preferred to carry out the pyrolysis under an elevated pressure.

The compound (5a) having a $R^{AF1}$O-group bonded to a vinyl fluoride group, has excellent polymerizability and thus is a compound useful as a material for a fluorocarbon resin. Such a compound (5a) may be polymerized, or the compound (5a) is copolymerized with a polymerizable monomer which is polymerizable with the compound (5a), whereby a useful polymer can be produced.

The polymerizable monomer which is polymerizable with the compound (5a), is not particularly limited and may be selected from known polymerizable monomers. As the method for the polymerization reaction, a known method for the reaction may be applied as it is. For example, in a case where the compound (5a) is a perfluoro (alkyl vinyl ether), the polymerizable monomer which is polymerizable with the compound (5a) may, for example, be a fluoroethylene such as $CF_2=CF_2$, $CF_2=CFCl$ or $CF_2=CH_2$, a fluoropropylene such as $CF_2=CFCF_3$, a (perfluoroalkyl)ethylene wherein the carbon number of the perfluoroalkyl group is from 4 to 12, such as $CF_3CF_2CF_2CF_2CH=CH_2$ or $CF_3CF_2CF_2CF_2CF=CH_2$, a vinyl ether having a group which can be converted to a carboxylic acid group or a sulfonic acid group, such as $CH_3OC(=O)CF_2CF_2CF_2OCF=CF_2$ or $FSO_2CF_2CF_2OCF(CF_3)CF_2OCF=CF_2$, or an olefin such as ethylene, propylene or isobutylene. The polymer obtained by the polymerization reaction, is useful as a fluorocarbon resin. The fluorocarbon resin is a useful functional material having an excellent property in the heat resistance and chemical resistance.

EXAMPLES

Now, the present invention will be described in detail with reference to Examples, but the present invention is by no means restricted to such Examples. In the following, gas chromatography will be referred to as GC, and gas chromatography mass analysis will be referred to as GC-MS.

Example 1

Example for Preparation of $CH_3CH_2CH_2OCH(CH_3)CH_2OCOCF(CF_3)OCF_2CF_2CF_3$ (3b) (Transesterification Step)

$CH_3CH_2CH_2OCH(CH_3)CH_2OH$ (hereinafter referred to as compound (2b), 20.0 g, 0.17 mol) was put into a flask and stirred while bubbling nitrogen gas. While maintaining the internal temperature at from 28 to 35° C., $CF_3CF_2CF_2OCF(CF_3)CF_2OCOCF(CF_3)OCF_2CF_2CF_3$ (hereinafter referred to as compound (1b), 67.4 g, 0.10 mol) was dropwise added over a period of 30 minutes. After completion of the dropwise addition, stirring was carried out at 50° C. for 2 hours, and further compound (1b) (22.5 g, 0.034 mol) was added. After completion of the addition, stirring was carried out at 35° C. for 3 hours to obtain 90.0 g of a crude liquid.

The obtained crude liquid was analyzed by GC, $^1$H-NMR and $^{19}$F-NMR, formation of $CH_3CH_2CH_2OCH(CH_3)CH_2OCOCF(CF_3)OCF_2CF_2CF_3$ (hereinafter referred to as "compound (3b)") was confirmed. The yield based on the compound (2b) calculated by $^1$H-NMR, was 99%.

Example 2

Example for Preparation of $CF_3CF_2CF_2OCF(CF_3)CF_2OCOCF(CF_3)OCF_2CF_2CF_3$ (1b) (Fluorination Step)

Compound (3b) (200.0 g) obtained in Example 1, was dissolved in $CF_3CF_2CF_2OCF(CF_3)COF$ (hereinafter referred to as compound (4b), 1000.0 g). On the other hand, into a 3000 mL autoclave made of nickel, NaF powder (260.5 g) was put, and compound (4b) (2000.0 g) was added, followed by stirring and cooling to −10° C. After supplying nitrogen gas for 1 hour, fluorine gas diluted to 20% with nitrogen gas, was supplied at a flow rate of 22.59 L/hr for 1 hour, and while supplying it at the same flow rate, the above fractional solution was injected over a period of 60 hours.

Then, while supplying fluorine gas diluted to 20% with nitrogen gas, while maintaining the above flow rate, 20 mL of a solution of compound (4b) in benzene (0.01 g/mL) was injected, the outlet valve of the autoclave was closed, and when the pressure became 0.12 MPa, the inlet valve of the autoclave was closed, followed by stirring for 1 hour. Further, such an operation was repeated 4 times during a period until the temperature rose from −10° C. to room temperature and thereafter 5 times at room temperature. During the period, benzene was supplied in a total of 1.800 g, and compound (4b) was injected in a total of 281.0 g. Thereafter, nitrogen gas was supplied for 2 hours, and the reaction mixture was taken out by decantation. The obtained crude liquid was concentrated by an evaporator, and the product was quantified by $^{19}$F-NMR, whereby it contained $CF_3CF_2CF_2OCF(CF_3)CF_2OCOCF(CF_3)OCF_2CF_2CF_3$ (compound (1b)) in a yield of 69%. A part of the crude liquid was taken and distilled under reduced pressure to obtain compound (1b). The boiling point of compound (1b) was from 46 to 51° C./5.2 kPa.

Example 3

Example for Preparation of Compound (1b) by a Continuous Process

Using compound (2b) (75.5 g, 0.640 mol) and compound (1b) obtained in Example 2 (213.1 g, 0.321 mol), the reaction was carried out in the same manner as in Example 1 to obtain compound (3b) (amount: 272.4 g, 0.634 mol). The yield of compound (3b) as quantified by $^1$H-NMR, was 99%. Then, the compound (3b) was reacted with fluorine in the same manner as in Example 2 to obtain compound (1b) (amount: 294.0 g, 0.44 mol). The same operation was repeated to finally obtain 3000 g of compound (1b).

Example 4

Example for Producing $CF_3CF_2CF_2OCF(CF_3)COF$ (4b) by Ester Dissociation (Liquid Phase Ester Dissociation Reaction)

Into a stainless steel autoclave having a capacity of 2 L and equipped with a stirrer, 1800 g of the crude liquid of compound (1b) obtained in Example 2 and further KF powder (30 g) prepared by a spray drying method, were charged and heated to 70° C. with stirring. When the temperature reached a prescribed level, the crude liquid of compound (1b) was continuously fed to the reactor at a rate of 115 g/hr. A generated gas was continuous withdrawn through a jacketed stainless steel column provided at an upper portion of the reactor, heated to 60° C. and captured by a dry ice trap. From the weight of the captured product and the analysis by GC, it was found that $CF_3CF_2CF_2OCF(CF_3)COF$ (compound (4b)) was formed at 110 g/hr. The yield of compound (4b) was 99%.

Example 5

Example for Preparation of a Dissociated Product (4b) of the Ester Bond of Compound (1b) (Gas Phase Ester Dissociation Reaction)

An empty U-letter type reactor made of inconel 600 (internal capacity: 200 mL) was immersed in a salt bath furnace maintained at 250° C. Nitrogen gas was supplied at a rate of 1 L/hr and compound (1b) obtained in Example 2 was supplied at a rate of 15 g/hr, from an inlet of the reactor. The retention time was maintained to be from 10 to 12 seconds. A crude gas of the reaction was recovered by providing dry ice/methanol and liquid nitrogen trap on the outlet side of the reactor. After the reaction for 2 hours, a liquid sample (23 g) was recovered from the trap. By GC-MS, compound (4b) was confirmed to be the main product. The NMR yield was 73%.

Example 6

Example for Preparation of $CF_3CF_2CF_2OCF=CF_2$ (5b) by Gas Phase Pyrolysis Step-2

A stainless steel column (inner diameter: 20 mm, length: 1 m) and a stainless steel fluidized bed reactor having an inner diameter of 45 mm and a height of 400 mm and packed with 280 g of $Na_2CO_3$ powder having an average particle size of 160 μm, were connected in series and installed in a salt bath, and the temperature in the salt bath was adjusted to 270° C. To the reactor, nitrogen gas was supplied at a rate of 1520 mL/min, and compound (4b) obtained in Example 5 was supplied at a rate of 60.2 g/hr for 1.8 hours by means of a metering pump. The product was recovered by installing a dry ice/ethanol trap at the outlet of the reactor. Compound (4b) was not detected, and it was found that $CF_3CF_2CF_2OCF=CF_2$ (hereinafter referred to as compound (5b)) was formed in a yield of 80%. The peaks by $^{19}F$-NMR (564.6 MHz, solvent: $CDCl_3$, standard: $CFCl_3$) of the product, agreed to the peaks of the standard product.

Example 7

Examples for Preparation of $CF_3CF_2CF_2OCF=CF_2$ (5b) by Gas Phase Pyrolysis Step-2

390 g of $Na_2CO_3$ powder was packed into a fluidized bed reactor comprising a hollow container (inner diameter: 51 mm, length: 400 mm) made of stainless steel and provided with upper and lower perforated plates (filtration precision: 0.5 μm, made of stainless steel). $Na_2CO_3$ used was one having a particle size within a range of from 100 to 250 μm. This reactor was installed in a molten salt bath heated to 260° C., and from the bottom of the reactor, nitrogen gas was supplied at a rate of 234 NL/hr for 8 hours to subject $Na_2CO_3$ to dehydration treatment. Thereafter, while maintaining the temperature of the reactor at 260° C., the crude liquid of compound (1b) having a purity of 95%, was diluted with nitrogen gas and continuously fed from the bottom of the reactor, and a gas discharged from the top of the reactor was liquefied and recovered by a dry ice trap. The feeding rates were adjusted so that the crude liquid of compound (1b) was 160 g/hr, and the nitrogen gas was 205 L/hr. The outlet gas of the reactor upon expiration of 2 hours from the initiation of the reaction, was analyzed by GC, whereby the conversion of compound (1b) was 83.2%, and the selectivity for compound (5b) was 95.2%. Further, the selectivity for compound (4b) was 0.8%. Further, upon expiration of 3 hours from the initiation of the reaction, the conversion of compound (1b) was 96.7%, and the selectivity for compound (5b) was 95.4%. Further, the selectivity for compound (4b) was 1.8%.

Example 8

Example for Preparation of Compound (1b) Employing Compound (2b) and Compound (4b)

Compound (2b) (620 g) was put into a 2 L autoclave made of hastelloy C and stirred, while bubbling nitrogen gas. While maintaining the internal temperature at from 25 to 35° C., compound (4b) (1830 g) was dropwise added over a period of 8 hours thereto. After completion of the dropwise addition, bubbling of nitrogen gas was further continued to remove HF and excess compound (4b) and to obtain 2245 g of compound (3b). Using compound (3b) (1800 g), a fluorination reaction was carried out in the same manner as in Example 2 to obtain compound (1b) in a yield of 69%.

INDUSTRIAL APPLICABILITY

According to the present invention, a fluorinated ester can be produced in a smaller number of reaction steps. Further, the process of the present invention is an effective process whereby the reaction yield is high, and the costs can be reduced. Further, a useful fluorinated acyl fluoride and a useful fluorinated vinyl ether can be produced in large amounts by using the fluorinated ester obtained by such a process.

The entire disclosure of Japanese Patent Application No. 2001-8252 filed on Jan. 16, 2001 including specification, claims and summary is incorporated herein by reference in its entirety.

What is claimed is:

1. A process for producing a fluorinated ester (1), comprising:
   reacting the following fluorinated ester (1) and the following compound (2) for transesterification to obtain the following compound (3), and
   fluorinating the compound (3) to obtain the fluorinated ester (1) in an amount larger than the molar amount prior to the transesterification:

$$R^{AF}-COOCF_2-R^{AF} \qquad (1)$$

$$R^A-CH_2OH \qquad (2)$$

$$R^{AF}-COOCH_2-R^A \qquad (3)$$

wherein $R^A$ is a monovalent organic group, and
$R^{AF}$ is the same group as $R^A$ or a monovalent organic group obtained by fluorination of $R^A$.

2. The process according to claim 1, wherein in the transesterification step, at most twice by mol of the compound (2) is reacted with the fluorinated ester (1) for transesterification.

3. The process according to claim 1, wherein the fluorination of the compound (3) is carried out by introducing fluorine gas into a liquid phase.

4. The process according to claim 1, wherein the fluorination of the compound (3) is carried out by introducing fluorine gas into a liquid phase having the fluorinated ester (1) or the following fluorinated acyl fluoride (4) dissolved therein:

$$R^{AF}\text{—COF} \tag{4}$$

wherein $R^{AF}$ is as defined above.

5. The process according to claim 1, wherein in the fluorination step, the compound (3) containing the following fluorinated acyl fluoride (4) and/or the compound (1) formed in the transesterification step, is used as it contains the fluorinated acyl fluoride (4) and/or the compound (1):

$$R^{AF}\text{—COF} \tag{4}$$

wherein $R^{AF}$ is as defined above.

6. The process according to claim 1, wherein the transesterification step is carried out in the absence of a solvent.

7. The process according to claim 1, wherein the fluorinated ester (1) in the transesterification step is the fluorinated ester (1) obtained in the fluorination step.

8. The process according to claim 1, wherein the fluorinated ester (1) used in the transesterification step is produced by a step of obtaining the following compound (3) by reacting the following fluorinated acyl fluoride (4) and the following compound (2), and fluorinating the obtained compound (3) in a liquid phase:

$$R^{AF}\text{—COF} \tag{4}$$

$$R^{A}\text{—CH}_2\text{OH} \tag{2}$$

$$R^{AF}\text{—COOCH2—R}^{A} \tag{3}$$

$$R^{AF}\text{—COOCF}_2\text{—R}^{AF} \tag{1}$$

wherein $R^{A}$ and $R^{AF}$ are as defined above.

9. A process for producing a fluorinated acyl fluoride (4), which comprises dissociating the ester bond of the following fluorinated ester (1) obtained by the process as defined in claim 1:

$$R^{AF}\text{—COOCF}_2\text{—R}^{AF} \tag{1}$$

$$R^{AF}\text{—COF} \tag{4}$$

wherein $R^{AF}$ is as defined above.

10. The process according to claim 1, wherein the fluorinated ester (1) is the following compound (1a), the compound (2) is the following compound (2a), the compound (3) is the following compound (3a), and $R^{AF}$ is $R^{AF1}\text{O—CF(CF}_3)\text{—}$:

$$R^{AF1}\text{O—CF(CF}_3)\text{—COOCF}_2\text{—CF(CF}_3)\text{—OR}^{AF1} \tag{1a}$$

$$R^{41}\text{O—CX}^1(\text{CX}^2\text{X}^3\text{X}^4)\text{—CH}_2\text{OH} \tag{2a}$$

$$R^{AF1}\text{O—CF(CF}_3)\text{—COOCH}_2\text{—CX}^1(\text{CX}^2\text{X}^3\text{X}^4)\text{—OR}^{41} \tag{3a}$$

wherein $R^{41}$ is a monovalent organic group, $R^{AF1}$ is the same group as said $R^{41}$ or a monovalent organic group obtained by fluorination of said $R^{41}$, and each of $X^1$, $X^2$, $X^3$ and $X^4$ which may be the same or different, is a hydrogen atom or a fluorine atom.

11. A process for producing a fluorinated vinyl ether (5a), comprising:
dissociating the ester bond of the following compound (1a) obtained by the process as defined in claim 10, to obtain the following compound (4a), and pyrolyzing the compound (4a):

$$R^{AF1}\text{O—CF(CF}_3)\text{—COOCF}_2\text{—CF(CF}_3)\text{—OR}^{AF1} \tag{1a}$$

$$R^{AF1}\text{O—CF(CF}_3)\text{—COF} \tag{4a}$$

$$R^{AF1}\text{O—CF=CF}_2 \tag{5a}$$

wherein $R^{AF1}$ is as defined above.

12. A process for producing a fluorinated vinyl ether (5a), which comprises pyrolyzing the following compound (1a) obtained by the process as defined in claim 10, at a temperature of at least 250° C.:

$$R^{AF1}\text{O—CF(CF}_3)\text{—COOCF}_2\text{—CF(CF3)—OR}^{AF1} \tag{1a}$$

$$R_{AF1}\text{O—CF=CF}_2 \tag{5a}$$

wherein $R^{AF1}$ is as defined above.

13. The process according to claim 1, wherein an equimolar amount of the compound (2) is reacted with the fluorinated ester (1) for transesterification to form an equimolar amount of the compound (3) and an equimolar amount of the fluorinated acyl fluoride (4) ($R^{AF}\text{COF}$), and then, the fluorinated acyl fluoride (4) is further reacted with an equimolar amount of the compound (2) to form an equimolar amount of the compound (3).

14. The process according to claim 1, wherein said monovalent organic group is a monovalent hydrocarbon group, a halogeno monovalent hydrocarbon group, a heteroatom-containing monovalent hydrocarbon group or a halogeno (heteroatom-containing monovalent hydrocarbon) group.

15. The process according to claim 1, wherein a temperature for the reaction of the fluorinated ester (1) and the compound (2) is at least −50° C. and at most +100° C.

16. The process according to claim 1, wherein an HF scavenger is present during said transesterification.

17. The process according to claim 1, wherein a reaction product of said transesterification comprises, in addition to the compound (3), unreacted fluorinated ester (1) and compound (2), and a fluorinated acyl fluoride (4):

$$R^{AF}\text{—COF} \tag{4}$$

wherein $R^{AF}$ is as defined above.

18. The process according to claim 1, wherein the fluorine content of the compound (3) is at least 30 mass %.

19. The process according to claim 1, wherein the molecular weight of compound (3) is 200 to 1000.

20. The process according to claim 1, wherein the reaction temperature for the fluorination reaction is at least −60° C. and at most the boiling point of the compound (3).

21. The process according to claim 1, wherein a temperature for the reaction of the fluorinated ester (1) and the compound (2) is at least −50° C. and at most the boiling point of a solvent used during the transesterification.

* * * * *

UNITED STATES PATENT AND TRADEMARK OFFICE
CERTIFICATE OF CORRECTION

PATENT NO. : 7,053,237 B2  Page 1 of 1
APPLICATION NO. : 10/619784
DATED : May 30, 2006
INVENTOR(S) : Okazoe et al.

It is certified that error appears in the above-identified patent and that said Letters Patent is hereby corrected as shown below:

On the title page, Item (54), and Column 1, line 1, the Title should read:

-- (54) PROCESSES FOR PRODUCING A FLUORINATED ESTER, A FLUORINATED ACYL FLUORIDE AND A FLUORINATED VINYL ETHER --

Signed and Sealed this

Fifteenth Day of August, 2006

JON W. DUDAS
*Director of the United States Patent and Trademark Office*